US00RE35880E

United States Patent [19]

Waldman et al.

[11] E Patent Number: Re. 35,880

[45] Reissued Date of Patent: Aug. 25, 1998

[54] ENDOCARDIAL ELECTRICAL MAPPING CATHETER AND METHOD

[75] Inventors: Lewis K. Waldman, La Jolla; Peng-Sheng Chen, La Canada-Flintridge, both of Calif.

[73] Assignee: Cardiac Pathways Corporation, Sunnyvale, Calif.

[21] Appl. No.: 518,355

[22] Filed: Aug. 13, 1995

Related U.S. Patent Documents

Reissue of:

[64] Patent No.: 5,237,996
Issued: Aug. 24, 1993
Appl. No.: 833,746
Filed: Feb. 11, 1992

[51] Int. Cl.[6] ..... A61B 5/042

[52] U.S. Cl. ..... 600/374

[58] Field of Search ..... 128/642; 607/122, 607/123, 128

[56] References Cited

U.S. PATENT DOCUMENTS

| | | | |
|---|---|---|---|
| Re. 32,204 | 7/1986 | Halvorsen | 128/642 |
| 3,856,009 | 12/1974 | Winnie | 128/214.4 |
| 4,501,276 | 2/1985 | Lombardi | 128/642 |
| 4,552,212 | 11/1985 | Gelinas et al. | 128/642 |
| 4,573,473 | 3/1986 | Hess | 128/642 |
| 4,602,645 | 7/1986 | Barrington et al. | 128/786 |
| 4,628,937 | 12/1986 | Hess et al. | 128/642 |
| 4,630,611 | 12/1986 | King | 128/642 |
| 4,641,664 | 2/1987 | Botvidsson | 128/785 |
| 4,649,924 | 3/1987 | Taccardi | 128/642 |
| 4,699,147 | 10/1987 | Chilson et al. | 128/642 |
| 4,777,955 | 10/1988 | Brayton et al. | 128/642 |
| 4,848,352 | 7/1989 | Phondorf et al. | 128/642 |
| 4,862,887 | 9/1989 | Weber et al. | 128/303.1 |
| 4,890,623 | 1/1990 | Cook et al. | 128/642 |
| 4,892,102 | 1/1990 | Astrinsky | 128/642 |
| 4,940,064 | 7/1990 | Desai | 128/784 |

FOREIGN PATENT DOCUMENTS 2565491 2/1995 France .

*Primary Examiner*—Lee S. Cohen
*Attorney, Agent, or Firm*—Flehr Hohbach Test Albritton & Herbert LLP

[57] ABSTRACT

An endocardial mapping catheter [for locating the ectopic focus of an abnormally functioning heart includes an actuator assembly and an elongated hollow support sheath which extends from the actuator assembly. A plurality of electrical probes are slidingly disposed for independent movement through the sheath, and each probe is attached to the actuator assembly for individual manipulation. A guide is mounted on the end of the sheath opposite the actuator assembly, at the distal end of the sheath, to radially deploy each electrical probe along a separate favorable trajectory as the probe is manipulated to move distally through the sheath. In operation, the probes are initially retracted into the sheath as the guide is positioned inside the left ventricle of the heart. Once the guide is positioned as desired, all of the probes are individually deployed until they have each made contact with the endocardium of the left ventricle. Timed responses are obtained from the probes, and a series of such responses from various guide locations in the left ventricle are recorded to accomplish circumferential endocardial mapping of the heart.] *comprising an elongate flexible support sheath having a proximal end and a distal end and a plurality of electrical probes. Each of the probes has a proximal end and a distal end and is slidably disposed in the support sheath. A guide is disposed on the distal end of the support sheath and has a plurality of passageways. Each of the passageways separately receives one of the probes and is formed with a surface having an arcuately extending distal portion. Actuators are carried by the proximal ends of the probes for deploying the distal ends of the probes from the support sheath. The arcuately extending distal portion of each surface serves to radially deploy the distal end of a probe from the guide along a favorable trajectory from the guide as the probe is individually moved distally through the support sheath.*

40 Claims, 3 Drawing Sheets

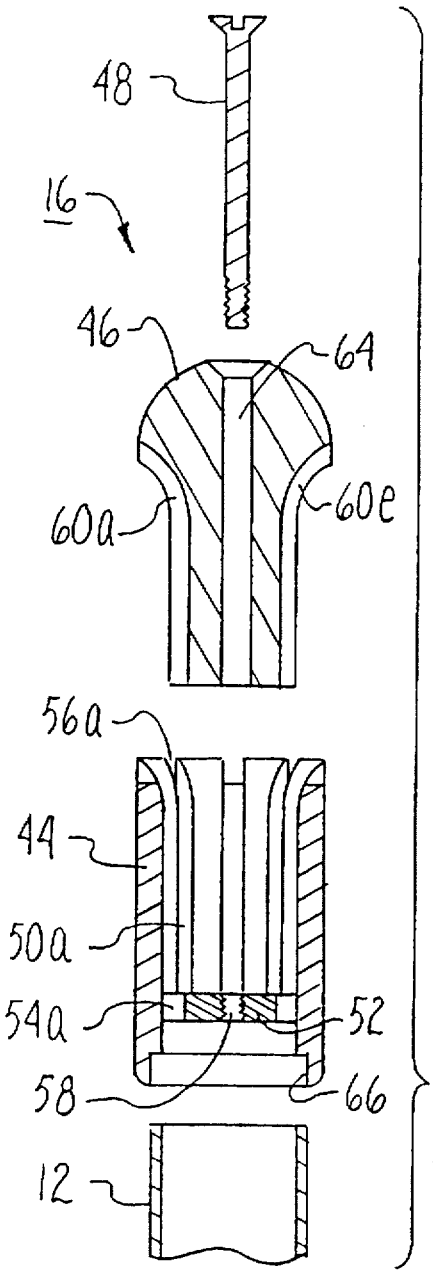
Fig. 2A
Fig. 2B
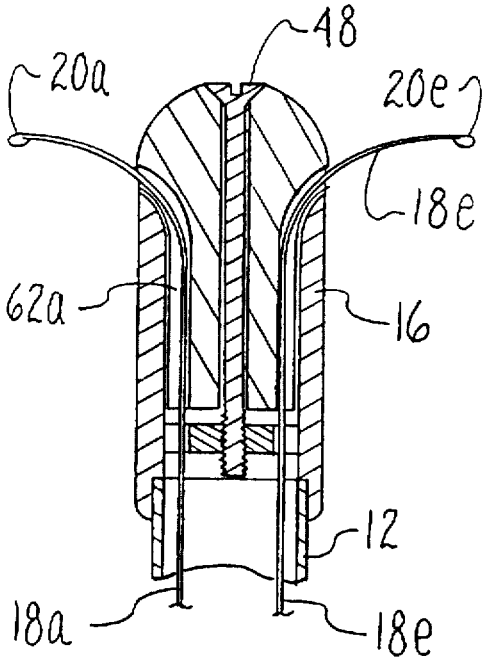

ENDOCARDIAL ELECTRICAL MAPPING CATHETER AND METHOD

Matter enclosed in heavy brackets [ ] appears in the original patent but forms no part of this reissue specification; matter printed in italics indicates the additions made by reissue.

FIELD OF THE INVENTION

The present invention pertains generally to diagnostic catheters. More particularly, the present invention pertains to a catheter which individually and selectively positions a plurality or electrodes at separate locations on the endocardium of the left ventricle of a heart to simultaneously record the electrical responses from these locations during contraction of the heart muscle. The present invention is particularly, but not exclusively, useful for the circumferential endocardial mapping of the left ventricle to locate the ectopic focus of an abnormally functioning heart muscle.

BACKGROUND OF THE INVENTION

As is well known, the heart muscle effectively acts as a pump which maintains the circulation of blood through the body. More particularly, the left ventricle is that portion of the heart which propels blood in systemic circulation through the body to supply the body tissues with nutrients. In lay terms, this pumping action results from contractions of the heart muscle which are more commonly referred to as the heart beat.

Normally, contractions of the heart muscle (i.e. heart beats) result from an excitation wave of electrical impulses which originate at the atrium, which propagate via the atrioventricular node to the ventricles, and which progress outwardly through conductive tissue in the endocardium. This is normal, and the rhythmic repetition of the heart beat is an indicator of good health. It happens, however, that for a diseased heart there are sometimes variations from the normal rhythm of the heart beat which are manifested as abnormal spontaneous contractions. These abnormalities are clinically referred to as arrhythmia, and they can cause numerous unwanted complications for a patient. Thus, for many reasons, it is desirable to locate the site of arrhythmogenesis or ectopic focus or an arrhythmia with the hope that medical intervention can cure the problem.

As is well known, the ectopic focus or an arrhythmia is usually located in the endocardium. This mislocation of the initiation of contraction from the atrium to what is now the ectopic focus is what causes the arrhythmia. Since heart contractions result from the progression of an excitation wave of electrical impulses location of the ectopic focus is merely a matter of identifying the point from where the abnormal excitation wave originates. Several catheter electrodes have been proposed for this purpose. The following specifically cited references are representative of these catheters.

U.S. Pat. No. 4,628,937 to Hess et al. for an invention entitled "Mapping Electrode Assembly" is an example of a device which is used for the epicardial or endocardial mapping of the electrical impulses from the heart. According to the teachings of the Hess et al. device, the electrodes are symmetrically arrayed within a mounting cup that conforms to the organ being mapped. Consequently the electrodes of the Hess et al. device are set relative to each other and the efficacy of their displacement is dependent on the ability of the cup to conform to the particular surface.

U.S. Pat. No. 4,699,147 to Chilson et al. for an invention entitled "Intraventricular Multielectrode Cardial Mapping Probe and Method for using Same" discloses a device which positions the electrodes along wire assemblies which can be extended from a catheter to create an elliptical envelope. This envelope is then incrementally rotatable within the heart chamber while electrical potentials are measured and recorded at different points on the endocardium. For this device, all of the electrodes are symmetrically deployed as a unit. Thus, there is no individual control over the placement of any given electrode. Further, there is no assurance that all or the electrodes have, in fact, made contact with the surface or the endocardium.

U.S. Pat. No. 4,522,212 Gelinas et al. for an invention entitled "Endocardial Electrode" discloses a plurality of spring legs having insulated conductors which are connected to respective sets of spaced electrodes. In operation these spring legs of the Gelinas et al. device are allowed to extend apart to cause the electrodes to engage the wall tissue. Again, as with the other above cited references, there is no individual control over each of the separate electrodes. Consequently, there is no assurance that each electrode is properly placed, or that there is even contact between the electrode and the endocardium.

None of the above examples either individually or collectively disclose the structure or the cooperation or structure which is used to accomplish the objects of the present invention.

In light of the above it is an object of the present invention to provide an endocardial mapping catheter which has a plurality of electrode probes which can each be independently manipulated to achieve non-axisymmetric placement of the electrodes against the endocardium of the left ventricle. Another object of the present invention is to provide an endocardial mapping catheter which establishes a favorable trajectory for each electrode during the placement process that directs the electrode into contact with the endocardium from a direction that is substantially perpendicular to the endocardium. Still another object of the present invention is to provide an endocardial mapping catheter which positions the plurality of electrodes circumferentially against the endocardium in a substantially coplanar arrangement. Yet another object of the present invention is to provide an endocardial mapping catheter which can be positioned, and repositioned, within the left ventricle of a heart to make successive recordings of electrical impulses from the endocardium for use in preparing an isochronal map or these impulses. Another object of the present invention is to provide an endocardial mapping catheter which is easy to use, relatively simple to manufacture and comparatively cost effective.

SUMMARY OF THE INVENTION

A catheter, for circumferentially mapping electrical responses from the left ventricle of the heart or a patient, includes a plurality of individually manipulable electrode probes which are structurally combined with an actuator assembly, a flexible support sheath and a probe guide. For the catheter of the present invention, the support sheath is a hollow elongated tube and the plurality of electrode probes are slidingly disposed inside the sheath. The actuator assembly is attached to the proximal end of the support sheath, and a plurality of actuation levers are slidably mounted on the actuator assembly. In addition to being slidably mounted on the actuator assembly, each of these levers is fixedly attached to the proximal end of one of the electrode probes. The probe guide, which is formed with a plurality of flared passageways is mounted on the distal end of the support sheath, and the distal end of each electrode probe is positioned to slide through one of the passageways of the guide.

In the operation of the endocardial mapping catheter of the present invention, the guide at the distal tip of the catheter is inserted into the left ventricle and positioned therein as desired. The operator then individually manipulates each actuation lever to move a respective electrode probe through the sheath in a distal direction. This action sequentially deploys all of the electrode probes through the guide of the catheter and into the left ventricle. In each case, the deployment of an electrode probe from the probe guide is accomplished along a favorable trajectory from the guide until the distal tip of the electrode probe contacts the endocardium. In accordance with the present invention, this favorable trajectory extends from the probe guide and into a line which is substantially perpendicular to the surface of the endocardium. All of the electrode probes are thus sequentially deployed radially from the guide to circumferentially position their respective distal tips against the endocardium in a substantially coplanar arrangement.

Once the distal tips or all electrode probes have been deployed into contact with the endocardium, the electrical responses resulting from heart muscle activity are recorded by electronic recording equipment associated with the catheter. After sufficient data have been obtained with the catheter in a particular position, the electrode probes can be withdrawn and the guide at the distal tip of the catheter can be repositioned as desired. Additional data can thus be obtained from several locations of the catheter in the left ventricle and an isochronal map can be developed from the recorded data. With this map, the site of arrhythmogenesis or ectopic focus on the heart can be located.

The novel features of this invention, as well as the invention itself, both as to its structure and its operation will be best understood from the accompanying drawings, taken in conjunction with the accompanying description, in which similar reference characters refer to similar parts, and in which:

BRIEF DESCRIPTION OF THE DRAWINGS

FIG. 2A is an exploded cross-sectional view of the guide of the catheter of the present invention as seen along the line 2—2 in FIG. 1A;

FIG. 2B is a cross-sectional view of the guide shown in FIG. 2A when assembled and with probes extending therethrough;

DESCRIPTION OF PREFERRED EMBODIMENTS

Figures 1A, 1B:
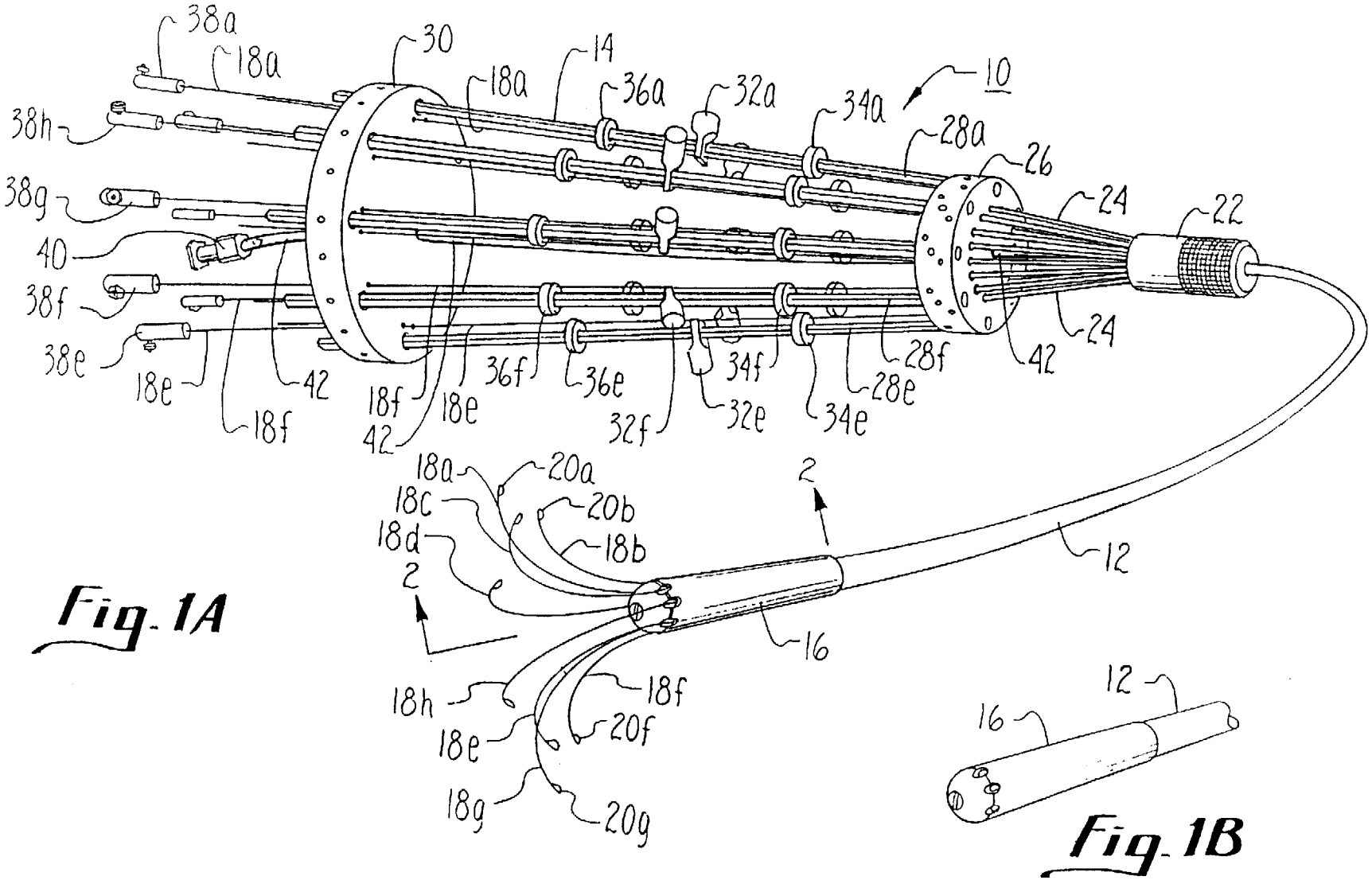
FIG. 1A is a perspective view of the endocardial electrical mapping catheter of the present invention.
FIG. 1B is a perspective view of the probe guide portion of the catheter when the probes of the catheter are retracted.

Referring initially to FIG. 1A, an endocardial mapping catheter in accordance with the present invention is shown and is generally designated 10. As shown, the catheter 10 includes a hollow elongated support sheath 12 which is formed with a lumen, and which is sufficiently flexible to be inserted through selected arteries of a body. An actuator assembly 14 is attached to the proximal end of the sheath 12, and a probe guide 16 is attached to its distal end. As indicated in FIG. 1A, a plurality of individual electrode probes 18 a–h, are disposed inside the hollow sheath 12 and extend therethrough from the actuator assembly 14 to the probe guide 16. It is to be appreciated that there may be any number of electrode probes 18 desired by the operator, and there is no reason for limiting the catheter 10 to the use or only eight such electrode probes 18 a–h as shown in the Figures. For brevity, individual probes may be referred to hereinafter as a probe 18.

FIG. 1A also shows that each electrode probe 18 has a tip 20 at its distal end. Preferably, the tip 20 is a bipolar electrode because electrical responses can be more clearly identified using a bipolar electrical structure. A unipolar tip 20, however, is within the contemplation of the present invention. Regardless what electrical structure is used for the electrode probes 18 a–h, it will be appreciated by cross referencing FIG. 1A with FIG. 1B that the catheter 10 is used to deploy the tips 20 of electrode probes 18 a–h from the probe guide 16. Specifically, it is the intention of the present invention that the electrode probes a–h be individually manipulable between a retracted configuration (shown in FIG. 1B) and a collectively deployed configuration (shown in FIG. 1A). The mechanics of how this is accomplished will be best appreciated by considering the actuator assembly 14 as it is shown in FIG. 1A.

First, FIG. 1A shows that a connector assembly 22 is used to join the actuator assembly 14 to the sheath 12. Next, a plurality of rigid spacer bars 24 are shown attached between the connector assembly 22 and a support disc 26. In turn, a plurality of rigid guide rods 28 a–h connect and position a base plate 30 relative to the support disc 26. It will be noticed in FIG. 1A that the guide rods 28 a–h are flared outwardly in the proximal direction from the support disc 26 toward the base plate 30. This is done to facilitate the manipulability of catheter 10. In any event, the connector assembly 22, support disc 26 and base plate 30, together with their respective interconnecting spacer bars 24 and guide rods 28 a–h, establish a rigid platform structure from which the individual electrode probes 18 of the catheter 10 can be manipulated.

Still referring to FIG. 1A, it will be seen that a plurality of actuation levers 32 a–h are slidably mounted on respective individual guide rods 28 a–h for movement between distal stops 34 a–h and proximal stops 36 a–h. Importantly, each guide rod 28 should have a cross section profile, such as a square or rectangle, which will prevent any rotation or the associated actuation lever 32 a–h about the longitudinal axis of the guide rod 28 a–h. As will also be appreciated by reference to FIG. 1A each of the actuation levers 32 a–h is fixedly attached to a respective electrode probe 18 a–h. Thus, any manipulation of the actuation levers 32 a–h between the distal stops 14 and the proximal stops 36 will result in a corresponding distal or proximal movement of the electrode probes 18 a–h. FIG. 1A also shows that an electrical connector 38 a–h is attached to the distal end of a respective electrode probe 18 a–h.

The catheter 10 also includes a nozzle 40 that is connected to a hose 42 which extends through the actuator assembly 14 and which is connected in fluid communication with the lumen of hollow support sheath 12. This nozzle 40 is attachable to a source of fluid (not shown), such as a saline solution, which can be used to flush the catheter 10 through the sheath 12 and probe guide 16 to help maintain its operability.

While the actuator assembly 14, as disclosed above, is important and necessary for manipulating the individual deployment of the electrode probes 18 a–h from the catheter 10, the trajectory which is followed by each electrode probe 18 a–h when it is deployed is, at least, of equal importance. The structure of catheter 10 which establishes the favorable trajectory of each electrode probe 18 is the probe guide 16. An understanding of the probe guide 16 will be best appreciated with reference to FIGS. 2A and 2B.

Referring first to the exploded view or guide probe 16 in FIG. 2A, it will be seen that guide probe 16 includes a base 44, and a head 46 which is held on the base 44 by a screw 48. More specifically, the base 44 is formed with a plurality of channels 50 a–h. Also, the base 44 has a bracket 52 which is formed with a plurality of holes 54 a–h that communicate respectively with the channels 50 a–h. As shown, each of the channels 50 a–h has a curved end 56 a–h, and the bracket 52 is formed with a threaded orifice 58. In an alternate embodiment, the base 44 can be made without the channels 50 a–h. On the other hand, the head 46 has a plurality of grooves 60 a–h which are formed to mate with the respective channels 50 a–h of the base 44 to create passageways 62 a–h (shown in FIG. 2B). To create these passageways 62 a–h, the screw 48 is inserted through the bore 64 of head 46 and threadably engaged with the threaded orifice 58 of base 44. This combination or components is, perhaps, best appreciated by reference to FIG. 2A. The sheath 12 can be joined to the detent 66 of base 44 by any means well known in the pertinent art, such as by solvent bonding.

OPERATION

Figure 3:
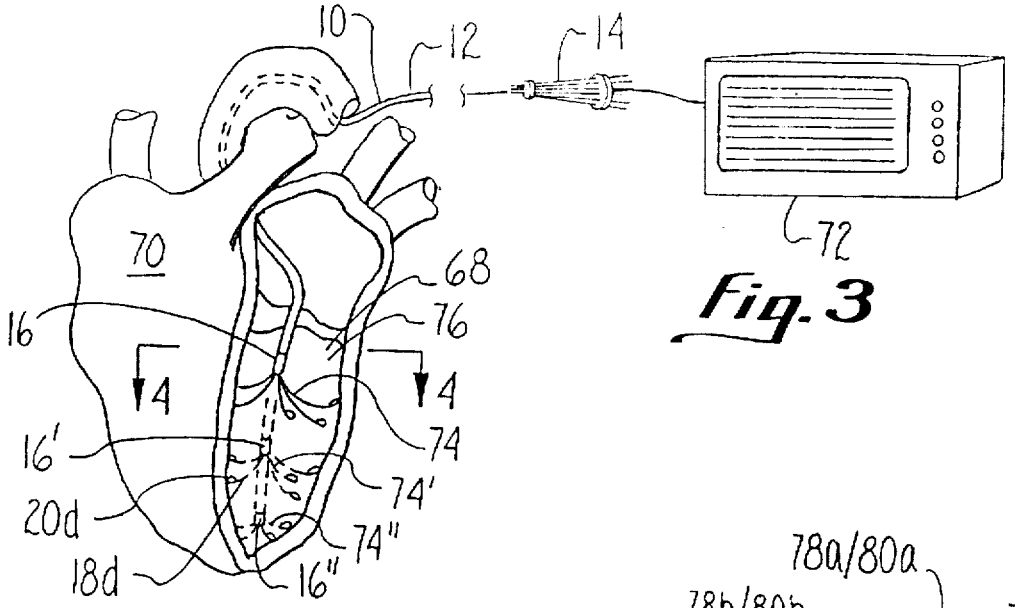
FIG. 3 is a perspective view of the heart of a patient with the catheter of the present invention inserted into the left ventricle, portions of the heart wall are removed for clarity and the guide is shown in phantom to indicate variations in the positioning of the guide inside the left ventricle of the heart.

In the operation of the endocardial mapping catheter 10 of the present invention, the catheter 10 is inserted into the left ventricle 68 of the heart 70 of a patient substantially as shown in FIG. 3. Additionally, FIG. 3 also shows the catheter 10 in its electrical connection with an electronic device 72. As will become more apparent, the electronic device 72 can be of any type well known in the pertinent art which is able to record the electrical signals from the heart 70 which are picked up by the various electrode probes 18 a–h.

FIG. 3 further indicates that the probe guide 16 at the distal end of catheter 10 can be moved and repositioned within the left ventricle 68. Specifically, FIG. 3 shows three different deployment patterns for the catheter 10 which are successively designated 74, 74' and 74". Importantly, for each deployment pattern 74, 74' or 74", the individual electrode probes 18 a–h are separately and individually extendable from the probe guide 16 along what is termed here, a favorable trajectory. Essentially, this is taken to mean that the tip 20 of any particular electrode probe 18 is deployed from the probe guide 16 along a path which approaches and contacts the endocardium 76 of the left ventricle 68 from a direction that is substantially perpendicular to the surface of the endocardium 76. The benefits to be obtained from this cooperation or structure are two-fold. First, it allows the electrode probe 18 to contact the endocardium from a direction which has the optimal probability of establishing a good electrical contact between the electrode probe 18 and the endocardium 76. Second, it allows the individual electrode probe 18 to continue to be deployed from the catheter 10 until there is such contact. A specific example will be instructive.

Consider the catheter 10 to be in the deployment pattern 74' as shown in FIG. 3. Further, consider that FIG. 4 corresponds to the positioning of the electrode probes 18 in deployment pattern 74'. Initially, when considering the electrode probes 18 a–h collectively, it can be appreciated that the deployed tips 20 a–h of the plurality of electrode probes 18 a–h are substantially coplanar when in contact with the endocardium 76. Next, when considering a specific electrode probe 18 (e.g. electrode probe 18d) it can be appreciated that the tip 20d of the electrode probe 18d contacts the endocardium 76 from a direction that is substantially perpendicular to the surface of the endocardium. Indeed, this is so for all electrode probes 18 a–h regardless of the topography of the endocardium 76 at the particular location where the tip 20 a–h makes its contact.

Figure 4:
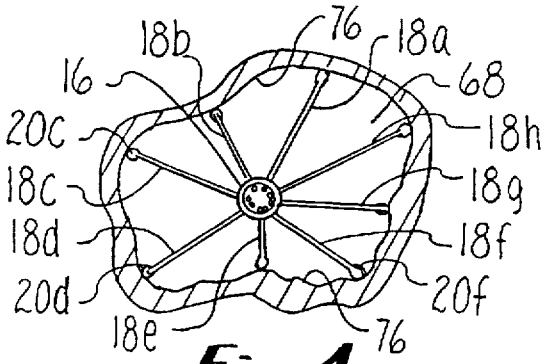
FIG. 4 is a cross-sectional view of the heart with inserted catheter as seen along the line 4—4 in FIG. 3.

Another important structural capability of the catheter 10 is that the location of probe guide 16 in left ventricle 68 need not be established with precision for any particular deployment pattern 74, 74' or 74". As shown in FIG. 4, the probe guide 16 is not centered in the left ventricle 68. Still, the various electrode probes 18 a–h are each capable of being deployed from the catheter 10 and into contact with the endocardium 76. For example, the electrode probe 18e is not deployed from probe guide 16 as far as is the electrode probe 18h. Nevertheless, both probes 18e and 18h are in contact with the endocardium 76.

From the above it will be appreciated that an operator can initially manipulate all of the actuation levers 32 a–h by drawing them proximally toward the proximal stops 36 a–h to withdraw the tips 20 of electrode probes 18 a–h into the retracted configuration for probe guide 16 shown in FIG. 1B. The probe guide 16 at the distal end of support sheath 12 can then be inserted into the left ventricle 68 using any approved medical procedure. Once the probe guide 16 is properly positioned inside the left ventricle 68 of heart 70 using well known techniques, such as by fluoroscopy, the electrode probes 18 a–h can be individually deployed along favorable trajectories into a deployment pattern 74. Electronic responses from the heart 70 can then be recorded by the electronic device 72. After a sufficient number of electronic responses has been recorded with catheter 10 in the deployment pattern 74, the electrode probes 18 a–h can be withdrawn into their retracted configuration. The probe guide 16 can then be repositioned within the left ventricle 68 for reconfiguration into the deployment pattern 74' and, subsequently from deployment pattern 74', into the deployment pattern 74". In each case, the operator is able to individually manipulate an actuation lever 32 on the actuator assembly 14 to either retract or deploy the corresponding electrode probe 18. Furthermore, during each deployment, the particular electrode probe 18 is deployed along a favorable trajectory.

Figure 5:
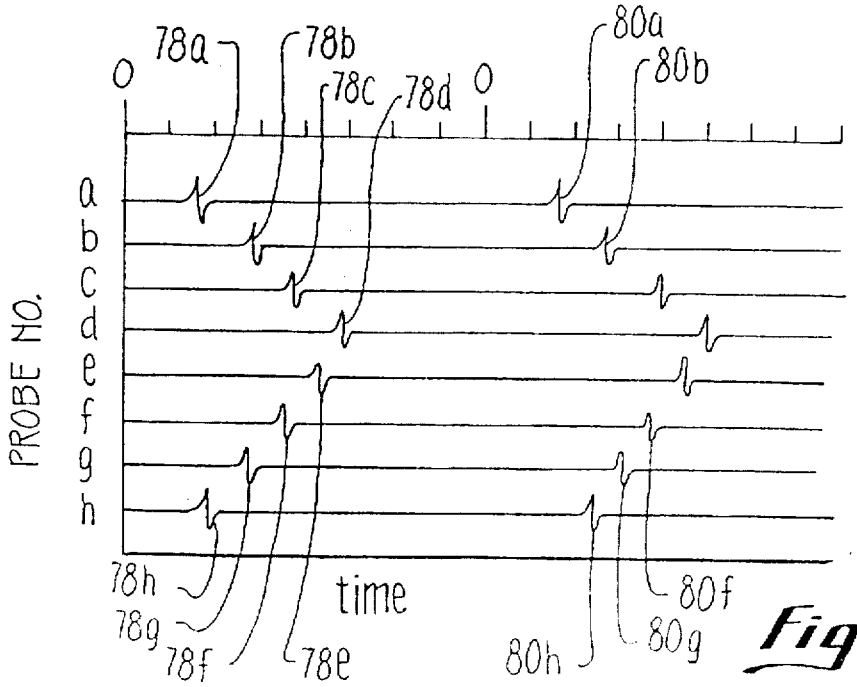
FIG. 5 is a representative graph of timed responses from each of the probes of the catheter of the present invention during sequential cardiac cycles.

FIG. 5 shows a representative time sequence of electrical responses resulting from contractions of the heart 70 as they would be received by the catheter 10 from the heart 70 during any particular deployment pattern 74. For a more specific example, consider that the catheter 10 is in the deployment pattern 74 shown in FIGS. 3 and 4. For the example of this deployment pattern 74, FIG. 5 shows that the recorded electrical responses 78 a–h, as obtained through the respective electrode probe 18 a–h, occur at different times. It happens that, because an arrhythmia occurs as waves, the earliest recorded response is nearer the ectopic focus. Thus, FIG. 5 indicates that for the particular contraction of heart 70 which caused the electrical responses 78 a–h, the electrode probes 18a and 18h were closest to the ectopic focus, and that the electrode probe 18d was farthest from the ectopic focus. Not surprisingly, the subsequent set of recorded electrical responses 80 a–h which are obtained by catheter 10 in this same deployment pattern 74 is substantially similar. Several such responses can be obtained, as desired by the operator. Among these responses recorded (78, 80), one will be chosen for analysis. The timing or the chosen activations relative to a selected reference time point, such as the onset of the QRS complex on the surface electrogram, will be assigned to one of the electrode locations shown in FIG. 6 marked 78a/80a to 78h/80h.

Figure 6:
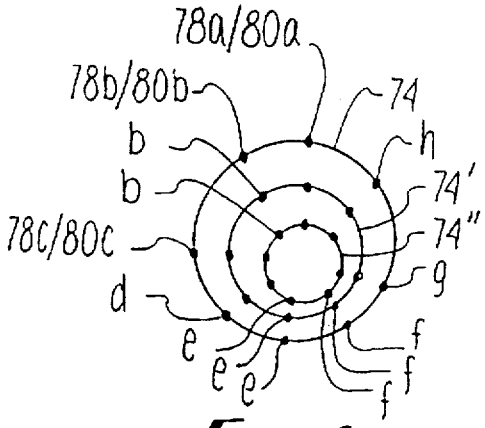
FIG. 6 is a representation of three locations from the apex to the base of the left ventricle at which responses were recorded during a procedure using the catheter of the present invention.

In FIG. 6 the electrical responses 78/80 a–h et seq. are plotted around the circumference designated to correspond with deployment pattern 74. Other circumferences are obtained corresponding to the deployment patterns 74' and 74", and the earliest responses are identified to locate the ectopic focus. In the contemplation of the present invention, as many deployment patterns may be accomplished as is deemed necessary by the operator to properly locate the site of arrhythmogenesis.

While the particular endocardial mapping catheter as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

We claim:

1. An endocardial mapping catheter which comprises:

an elongated flexible support sheath having a proximal end and a distal end, said sheath having a lumen extending lengthwise therethrough;

a plurality of electrical probes, each of said probes having a proximal end and a distal end and being slidably disposed in said lumen;

a guide attached to said distal end of said support sheath, said guide having a plurality of passageways separately receiving one said probe to radially deploy said distal end of each said probe along a favorable trajectory from said guide as each said probe is individually moved distally through said lumen and said passageway;

a plurality of guide rods, each said guide rod having a distal end and a proximal end; and a plurality of actuation levers, each said actuation lever being slidably mounted on one of said guide rods and fixedly attached to one of said probes for moving said probe to deploy said distal end of said probe.

2. A catheter as recited in claim 1 for measuring electrical responses from the endocardium of the left ventricle of the heart of a patient to ascertain the origin of an arrhythmia, wherein each said rod has a substantially rectangular cross-section and each said actuation lever is engageable with a respective said rod and is manipulable to individually and selectively deploy each said electrical probe into contact with the endocardium of the left ventricle to simultaneously measure said electrical responses from each said probe on substantially coplanar portions of the endocardium.

3. A catheter as recited in claim 2 further comprising means for recording said electrical responses.

4. A catheter as recited in claim 3 further comprising means for outwardly flaring said guide rods in a proximal direction to facilitate manipulation of said actuation levers.

5. A catheter as recited in claim 4 wherein said flaring means comprises a base attached to said distal ends of said plurality of guide rods, and a flaring disc distanced from said base and attached to said proximal ends of said plurality of guide rods.

6. A catheter as recited in claim 5 further comprising means for injecting fluid through said lumen of said support sheath and through said plurality of passageways in said guide.

7. A catheter as recited in claim 6 further comprising a plurality of electrical connectors, each said electrical connector being attached to one of said proximal ends of said probes for establishing an electrical connection between said probe and said means for recording said electrical responses.

8. A catheter as recited in claim 7 wherein at least one of said probes is a bi-polar wire.

9. An endocardial mapping catheter for determining electrical responses from portions of the endocardium of the left ventricle of the heart of a patient to ascertain the original of an arrhythmia which comprises:

a plurality of electrode probes wherein each of said probes has a proximal end and a distal end;

means for collectively inserting said probes into said left ventricle;

means for individually and selectively deploying each said electrode probe into contact with said endocardium to circumferentially measure said electrical responses from each said probe on substantially coplanar portions of said endocardium;

a plurality of guide rods, each said guide rod having a distal end and a proximal end; and a plurality of actuation levers, each said actuation lever being slidably mounted on one of said guide rods and fixedly attached to one or said probes for moving said probe to deploy said distal end of said probe.

10. A catheter as recited in claim 9 wherein said means for collectively inserting said probes into said left ventricle is an elongated flexible support sheath having a proximal end and a distal end, said sheath having a lumen extending lengthwise therethrough, and wherein each or said probes is slidably disposed in said lumen.

11. A catheter as recited in claim 10 wherein said means for deploying each said probe comprises a guide attached to said distal end of said support sheath, said guide having a plurality of passageways separately receiving one said probe and radially deploying said distal end of each said probe along a favorable trajectory as each said probe is individually moved distally said lumen and through said passageway.

12. A catheter as recited in claim 11 further comprising means for outwardly flaring said guide rods in a proximal direction to facilitate manipulation of said actuation levers, said flaring means including a base attached to said distal ends or said plurality of guide rods, and a flaring disc distanced from said base and attached to said proximal ends of said plurality of guide rods.

13. A catheter as recited in claim 12 wherein said guide rods have substantially rectangular cross sections to inhibit rotation of fluid actuation levers and said probes, and said catheter further comprises means for injecting fluid through said lumen of said support sheath and through said plurality of passageways in said guide.

14. A catheter as recited in claim 13 further comprising a means for recording said electrical responses and a plurality or electrical connectors, each said electrical connector being attached to one of said proximal ends of said probes for establishing an electrical connection between said probe and said means for recording said electrical responses.

15. A catheter as recited in claim 14 wherein at least one of said probes is a bi-polar wire.

16. A method for measuring electrical responses from portions of the endocardium of the left ventricle of the heart of a patient to ascertain the origin of an arrhythmia using an endocardial mapping catheter comprising a hollow elongated flexible support sheath having a proximal end and a distal end, a plurality of electrical probes slidably disposed in the sheath, each said probe having a distal end, a guide attached to the distal end of the support sheath to radially deploy the distal ends of the probes along a favorable trajectory as each probe is individually moved distally through the support sheath, the catheter further comprising an actuator assembly having a plurality of guide rods and a plurality of actuation levers with each lever slidably mounted on one of the guide rods and fixedly attached to one of the probes for moving the probe to deploy the distal end of the probe; the method comprising the steps of:

A) selectively positioning said guide of said support sheath in said left ventricle;

B) individually deploying said probes to establish electrical contact between said probes and said endocardium of said left ventricle;

C) recording electrical responses from said endocardium through said probes for a selected number of cardiac cycles;

D) withdrawing said probes into said sheath;

E) repositioning said guide in said left ventricle to repeat steps B, C, and D, as necessary; and F) mapping the [recording] *recorded* electrical responses from said endocardium to locate the site of arrhythmogenesis.

17. A method as recited in claim 16 wherein said deploying step is accomplished by sequentially extending substantially diametrically opposite probes, in pairs, until all said probes are placed in contact with the endocardium for circumferential endocardial mapping.

*18. An endocardial mapping catheter which comprises an elongate flexible support sheath having a proximal end and a distal end, a plurality of probes, each of said probes having a proximal end and a distal end and being slidably disposed in said support sheath, at least one electrode mounted on the distal end of each probe, guide means disposed on said distal end of said support sheath for directing the probes from the sheath, said guide means having a plurality of passageways, each of said passageways separately receiving one of said probes and being formed with a surface having an arcuately extending distal portion, means carried by the proximal ends of said probes for deploying the distal ends of said probes from said support sheath whereby the arcuately extending distal portion of each surface serves to radially deploy said distal end of a probe from said guide means along a favorable trajectory from said guide means as said probe is moved distally through said support sheath.*

*19. A catheter as in claim 18 for sensing electrical signals from the endocardium of a heart of a patient wherein said means carried by the proximal ends of said probes is manipulatable to individually and selectively deploy each probe into contact with the endocardium to sense said electrical signals with the electrodes.*

*20. A catheter as in claim 19 further comprising means for recording said electrical signals.*

*21. A catheter as in claim 20 further comprising a plurality of electrical connectors, each said electrical connector being attached to one of said proximal ends of said probes for establishing an electrical connection between said probe and said means for recording said electrical signals.*

*22. A catheter as in claim 18 wherein at least one of said probes is a bipolar wire.*

*23. An endocardial mapping catheter for sensing electrical signals from portions of an endocardium of a heart of a patient comprising a plurality in excess of two probes, each of said probes having a proximal end portion and a distal end portion, at least one electrode mounted on the distal end portion of each probe, introducer means having proximal and distal extremities and at least one lumen extending between the proximal and distal extremities for collectively inserting said probes into the heart and means secured to the proximal end portion of each probe for individually and selectively moving said probe in the at least one lumen so as to deploy the probe into contact with the endocardium and measure electrical signals picked up by the at least one electrode mounted on the distal end portion of each probe on spaced apart portions of the endocardium.*

*24. A catheter as in claim 23 wherein said introducer means is an elongate flexible support sheath.*

*25. A catheter as in claim 24 wherein said support sheath is provided with a plurality of spaced apart openings in the distal extremity, each of said probes being disposed in a separate opening.*

*26. A catheter as in claim 24 further comprising guide means formed on the distal extremity of said support sheath for directing the probes from the sheath, said guide means having a plurality of passageways, each passageway separately receiving one of said probes and radially deploying said distal end portion of the probe along a favorable trajectory as the probe is individually moved distally through said passageway.*

*27. A catheter as in claim 26 further comprising means for recording said electrical signals and a plurality of electrical connectors, each electrical connector being attached to one of said proximal end portions of said probes for establishing an electrical connection between said probe and said means for recording said electrical signals.*

*28. A catheter as in claim 27 wherein at least one of said probes is a bipolar wire.*

*29. A method for sensing electrical signals from portions of an endocardium of a chamber of a heart of a patient to ascertain the origin of an arrhythmia using an endocardial mapping catheter comprising an elongate flexible support sheath having a proximal end and a distal end, a plurality of electrical probes slidably disposed in said sheath, each probe having a distal end, guide means provided on the distal end of the support sheath to radially deploy the distal ends of the probes along a favorable trajectory as each probe is moved distally through the support sheath and means secured to each of the probes for moving the probe to deploy the distal end of the probe, the method comprising the steps of (a) selectively positioning said guide means of said support sheath in the chamber, (b) deploying said probes to establish electrical contact between said electrodes and the endocardium of the chamber, (c) recording electrical signals from the endocardium through said probes for a selected number of cardiac cycles, (d)* withdrawing said probes into said sheath,*(e) repositioning said guide means in the chamber to repeat steps (b) (c) and (d) as necessary and (f) mapping the recorded electrical signals from the endocardium to locate the site of arrhythmogenesis.*

*30. A method as in claim 29 wherein said deploying step is accomplished by sequentially extending substantially diametrically opposite probes in pairs until all said electrodes*

*are placed in contact with the endocardium for circumferential endocardial mapping.*

*31. An endocardial mapping catheter for sensing electrical signals from portions of an endocardium of a heart of a patient comprising a body having proximal and distal extremities, said body having a plurality of spaced apart passageways extending therethrough to respective openings at the distal extremity of said body, a plurality of mapping probes having proximal and distal end portions, each of said mapping probes being slidably mounted in said body and extending through a separate passageway in said body, at least one electrode mounted on the distal end portion of each mapping probe and means secured to the proximal end portions of said mapping probes for individually moving said mapping probes in said passageways to move the distal end portions of said mapping probes from the distal extremity of said body into the heart of the patient so that the electrodes can sense electrical signals from the endocardium and thus ascertain the origin of an arrhythmia.*

*32. A catheter as in claim 31 wherein the passageways in said distal extremity of the body are positioned so that they exit from the body to provide a favorable trajectory for each mapping probe as it is individually moved through the passageway in the body.*

*33. A catheter as in claim 32 wherein said passageways in said body are disposed so that the distal end portions of the mapping probes engage the endocardium in circumferentially spaced apart positions disposed substantially in a single plane.*

*34. A catheter as in claim 31 further comprising means for simultaneously recording electrical signals received by the mapping probes from the endocardium of the heart.*

*35. A method for mapping the endocardium of a heart of a patient accessible through a vessel of the patient by the use of a sheath having a distal extremity with a plurality of spaced apart openings therein and a plurality of separate mapping probes having proximal and distal extremities, at least one electrode mounted on the distal extremity of each mapping probe, comprising introducing the sheath into the vessel of the patient, introducing the plurality of mapping probes into the sheath and through the openings, individually moving each mapping probe through a separate opening, moving the distal extremities of the mapping probes into contact with the endocardium and sensing the electrical signals from the endocardium of the heart with the electrodes mounted on the distal extremities of the mapping probes.*

*36. A method as in claim 35 further comprising the step of recording simultaneously the signals sensed by the electrodes.*

*37. A method as in claim 35 further comprising the step of positioning the distal extremities of the mapping probes on the endocardium so that they contact the endocardium in circumferentially spaced apart positions lying substantially in a single plane.*

*38. A method as in claim 37 further comprising repositioning the distal extremities of the mapping probes so that they lie in circumferentially spaced apart positions lying substantially in another single plane spaced apart from said first named single plane and thereafter sensing electrical signals in the another single plane with the electrodes.*

*39. A method for mapping an endocardium in a chamber of a heart of a patient by the use of a sheath having a distal extremity and a plurality of separate probes having distal extremities, at least one electrode mounted on the distal extremity of each probe, comprising introducing the sheath into the body of the patient, introducing the probes into the sheath so that each probe extends through the sheath, individually deploying each of the probes from the distal extremity of the sheath into the chamber of the heart, moving the distal extremities of the probes into contact with portions of the endocardium and measuring the electrical signals picked up by the electrodes mounted on the distal extremities of the probes from the endocardium of the heart.*

*40. A method as in claim 39 using a plurality in excess of two probes.*

* * * * *